United States Patent
Messaoud et al.

(10) Patent No.: US 11,328,793 B2
(45) Date of Patent: *May 10, 2022

(54) ACCELERATING GENOMIC DATA PARSING ON FIELD PROGRAMMABLE GATE ARRAYS

(71) Applicant: INTERNATIONAL BUSINESS MACHINES CORPORATION, Armonk, NY (US)

(72) Inventors: Safa Messaoud, Sfax (TN); Takeshi Ogasawara, Tokyo (JP)

(73) Assignee: International Business Machines Corporation, Armonk, NY (US)

( * ) Notice: Subject to any disclaimer, the term of this patent is extended or adjusted under 35 U.S.C. 154(b) by 176 days.

This patent is subject to a terminal disclaimer.

(21) Appl. No.: 16/668,166

(22) Filed: Oct. 30, 2019

(65) Prior Publication Data
US 2020/0066373 A1    Feb. 27, 2020

Related U.S. Application Data

(63) Continuation of application No. 15/259,141, filed on Sep. 8, 2016, now Pat. No. 10,522,241.

(51) Int. Cl.
*G16B 20/00* (2019.01)
*G16B 20/20* (2019.01)
(Continued)

(52) U.S. Cl.
CPC ............. *G16B 20/20* (2019.02); *G16B 20/00* (2019.02); *G16B 30/10* (2019.02); *G16B 50/50* (2019.02); *G16B 30/00* (2019.02); *G16B 50/00* (2019.02)

(58) Field of Classification Search
None
See application file for complete search history.

(56) References Cited

U.S. PATENT DOCUMENTS

| | | | |
|---|---|---|---|
| 9,098,490 B2 | 8/2015 | Park et al. | |
| 2004/0028227 A1* | 2/2004 | Yu | H04L 63/0478 380/201 |

(Continued)

FOREIGN PATENT DOCUMENTS

| | | |
|---|---|---|
| CN | 103546160 | 1/2014 |
| WO | 2008/138008 | 11/2008 |

OTHER PUBLICATIONS

Cargo: effective format-free compressed storage of genomic information, Roguski et al (Year: 2016).*

(Continued)

*Primary Examiner* — Augustine K. Obisesan
(74) *Attorney, Agent, or Firm* — Tutunjian & Bitetto, P.C.; Randall Bluestone

(57) ABSTRACT

Methods and systems for accelerated input data conversion include partially parsing an input data set to convert the data set from a first format to a second format in an intermediate output having at least one unparsed portion to quickly perform a majority of the conversion. The partial parsing operates on portions of the input data set having a size less than a threshold size and leaves portions of the input data having a size greater than the threshold size unparsed. The intermediate output is parsed to convert at least one unparsed portion from the first format to the second format in a final output to complete the conversion such that a combined parsing time of the partial parse of the input data set and the parse of the intermediate output is accelerated relative to a single-stage parsing.

20 Claims, 3 Drawing Sheets

(51) Int. Cl.
  *G16B 50/50* (2019.01)
  *G16B 30/10* (2019.01)
  *G16B 50/00* (2019.01)
  *G16B 30/00* (2019.01)

(56) References Cited

U.S. PATENT DOCUMENTS

| | | | | |
|---|---|---|---|---|
| 2007/0160208 | A1* | 7/2007 | MacLean | H04N 7/1675 380/210 |
| 2010/0095114 | A1* | 4/2010 | Greene | H04L 65/601 713/160 |
| 2010/0306398 | A1* | 12/2010 | Chang | H04L 69/22 709/230 |
| 2012/0020475 | A1* | 1/2012 | Altmann | H04L 9/36 380/42 |
| 2014/0114929 | A1 | 4/2014 | Henrichs et al. | |
| 2015/0379276 | A1* | 12/2015 | Glickman | G06F 21/602 713/193 |

OTHER PUBLICATIONS

Manual Reference Pages—bwa (1), http://bio-bwa.sourceforge.net/bwa.shtrnl, May 31, 2016.

Vasudevan Rengasamy, Engineering a high-performance SNP detection pipeline, Penn State Computer Science and Engineering Technical Report, Apr. 2015.

Hasitha Muthumala Waidyasooriya, Hardware-Acceleration of Short-read Alignment Based on the Burrows-Wheeler Transform, in IEEE Transactions on Parallel and Distributed Systems, vol. 27, No. 5, pp. 1358-1372, May 1, 2016.

Anoynomous, Sequence Alignment/Map Format Specification, The SAM/BAM Formal Specification Working Group, Nov. 18, 2015.

List of IBM Patents or Patent Applications Treated as Related dated Oct. 30, 2019, 2 pages.

* cited by examiner

ACCELERATING GENOMIC DATA PARSING ON FIELD PROGRAMMABLE GATE ARRAYS

BACKGROUND

Technical Field

The present invention generally relates to genomic data processing and, more particularly, to processing genomic data using hardware with hardware resource limitations.

Description of the Related Art

Reading genomic data generates very large amounts of information. As genome sequencers improve, ever larger genome data files are created (e.g., on the order of terabytes). A de facto standard for storing this information is the sequence alignment/map (SAM) format, which is a tab-delimited text format. Gene sequences in SAM files are stored as lines of plain text, with each line having eleven mandatory fields and any number of optional fields. As a result, the length of lines in a SAM file can be variable, with some lines being much longer than others.

Parsing a SAM file involves reading a byte stream of the SAM file, splitting it into fields, and converting the information in the fields from text to binary. This parsing is a potential performance bottleneck in software tools that process genome files on, e.g., multiprocessor systems. If SAM parsing produces the binary data efficiently, other components can analyze and process the data with full processor utilization. SAM processing can be slow due to the sequential code that includes many complex branches.

SUMMARY

A method for accelerated input data conversion include partially parsing an input data set to convert the data set from a first format to a second format in an intermediate output having at least one unparsed portion to quickly perform a majority of the conversion. The partial parsing operates on portions of the input data set having a size less than a threshold size and leaves portions of the input data having a size greater than the threshold size unparsed. The intermediate output is parsed to convert at least one unparsed portion from the first format to the second format in a final output to complete the conversion such that a combined parsing time of the partial parse of the input data set and the parse of the intermediate output is accelerated relative to a single-stage parsing.

A method for accelerated input data conversion includes partially parsing an input data set using a dedicated hardware component to convert the data set from a sequence alignment/map (SAM) format to a second format in an intermediate output having at least one unparsed portion to quickly perform a majority of the conversion. The partial parse operates on portions of the input data set having a size less than a threshold size and leaves portions of the input data having a size greater than the threshold size unparsed and wherein a size of the intermediate output, including the at least one unparsed portion, is allocated based on a size of the unparsed input data set. A marker is embedded in the intermediate output indicating a location of the unparsed portion in the input data set. The intermediate output is parsed using a software processing module executed by a hardware processor to convert at least one unparsed portion from the first format to the second format in a final output to complete the conversion such that a combined parsing time of the partial parse of the input data set and the parse of the intermediate output is accelerated relative to a single-stage parsing.

A system for accelerated input data conversion includes a first parsing module including a hardware processor configured to partially parse an input data set to convert the data set from a first format to a second format in an intermediate output having at least one unparsed portion to quickly perform a majority of the conversion. The first parsing module operates on portions of the input data set having a size less than a threshold size and leaves portions of the input data having a size greater than the threshold size unparsed. A second parsing module is configured to parse the intermediate output to convert at least one unparsed portion from the first format to the second format in a final output to complete the conversion such that a combined parsing time of the partial parse of the input data set and the parse of the intermediate output is accelerated relative to a single-stage parsing.

These and other features and advantages will become apparent from the following detailed description of illustrative embodiments thereof, which is to be read in connection with the accompanying drawings.

BRIEF DESCRIPTION OF THE DRAWINGS

The disclosure will provide details in the following description of preferred embodiments with reference to the following figures wherein.

DETAILED DESCRIPTION

Embodiments of the present invention provide efficient hardware acceleration of sequence alignment/map (SAM) files. In particular, the present embodiments may use power-efficient parallel data converters implemented in hardware to speed up SAM parsing.

One option for such hardware acceleration is to use field programmable gate arrays. These devices can parse SAM fields more efficiently that software implementations. However, because of the variable length of SAM inputs, one challenge that arises is how to parse the entire input data in view of limited hardware resources. The present embodiments address this challenge by parsing input lines up to a threshold number of fields using hardware acceleration. For any lines that exceed a threshold dictated by available hardware resources, the accelerator skips the line and generates error information. Subsequent software parsing locates any errors in the output of the hardware acceleration, locates the original input information, and performs a slower, but more flexible conversion on only those unparsed regions.

Figure 1:
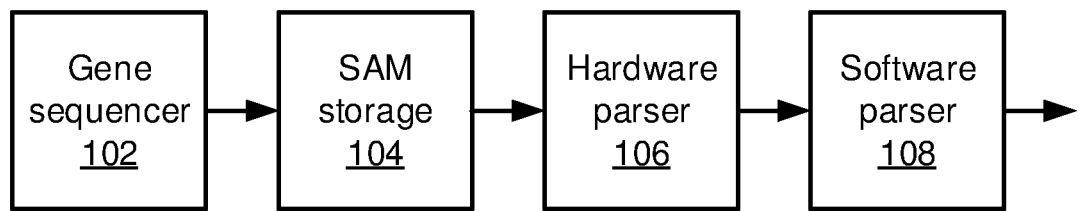
FIG. 1 is a block diagram of a system for accelerated conversion of sequential alignment/map (SAM) input information to another format in accordance with embodiments of the present invention.

Referring now to FIG. 1, a system flow of SAM parsing is shown. It should be understood that the system of FIG. 1 is intended only to illustrate functional components. The components shown in FIG. 1 may be implemented all as components of a single device or may be separate devices.

A gene sequencer 102 analyzes genetic material and generates genetic sequences. A genetic sequence is generally indicated by designations of base pairs, with the nucleotides being indicated by respective letters. The nucleotides generally present in DNA are adenine, cytosine, guanine, and thymine, with uracil replacing thymine in RNA sequences. The genetic sequences are therefore generally represented by strings of the letters ACGT (or ACGU, for RNA). Other nucleotides and designations within the sequences are possible, including degenerate nucleotides and unnatural nucleotides. The gene sequencer 102 outputs the gene sequences in SAM format and stores them in SAM store 104. The stored SAM sequences can have additional information stored in the optional fields of the SAM format.

A hardware parser 106 performs a first pass at parsing the stored SAM information. The hardware parser 106 converts the SAM information to a binary format such as, e.g., BAM (a binary/compressed version of the text-based SAM format). It is specifically contemplated that the hardware parser 106 may be implemented as a field programmable gate array (FPGA), though it should be understood that other hardware implementations may be used, such as application specific integrated chips. The hardware parser 106 may have certain fixed resource limitations, such that there may be lines of SAM information that the hardware parser 106 cannot convert. The hardware parser 106 outputs error information for such lines, identifying the location within the input where the error occurred, before moving on to the next line of SAM information.

A software parser 108 then processes the output of the hardware parser 106. For lines which have already been converted to BAM format, the software parser 108 skips over them to the next line. For lines that are marked as having errors, the software parser 108 performs the conversion of the input information to the output format and allocates any additional resources it may need to accommodate all of the fields in the original formal.

It should be recognized that, although SAM and BAM are specifically described herein as the input and output formats, the present embodiments may be employed to effectively accelerate any format conversion from an input format that comes in chunks of varying size. By applying the hardware parser 106 to those portions of the input that are within a threshold size, the speed of parsing can be increased substantially. The threshold is selected such the threshold will be exceeded rarely enough that the overhead imposed by the software parser 108 will be significantly outweighed by the hardware acceleration gains.

Figure 2:
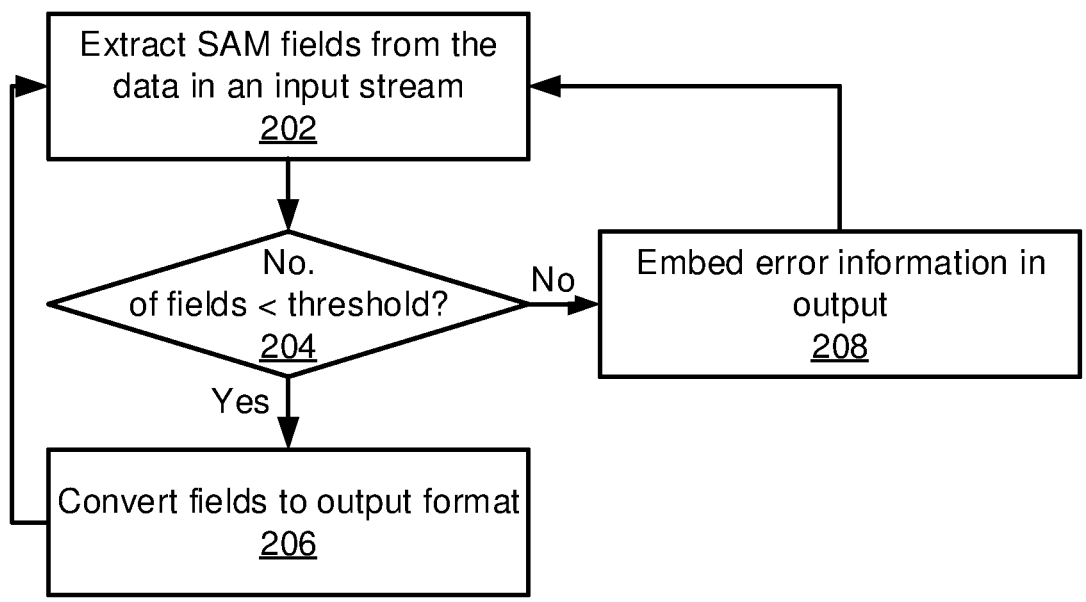
FIG. 2 is a block/flow diagram of a method for first-stage parsing of SAM input information in accordance with embodiments of the present invention.

Referring now to FIG. 2, a method of hardware parsing an input format to an output format in the hardware parser 106. Block 202 extracts SAM fields from the data in an input stream. As noted above, SAM is a tab delimited format, so extraction of fields may include tokenizing the lines of the SAM input data based on tabs. Other formats may be broken up into fields in a similar way according to the respective specifications of those formats. Block 204 determines whether the number of fields in a given line of input data is below a threshold number. If so, block 206 converts the fields to an output format and adds the information to an output stream. As noted above, it is specifically contemplated that BAM can be used the format of the output stream, but any appropriate data format can be used instead. If not, block 208 embeds error information in the output stream. Processing returns to block 202 to receive the next line of input data.

The threshold value is determined by the hardware resources available on the hardware parser 106. While arbitrary numbers of fields can be accommodated, doing so increases the size, complexity, and cost of the hardware accelerator 106. As such, the hardware accelerator is designed with reasonable limits. The threshold value may be determined based on a statistical analysis of how many fields are generally included in target inputs, with a balance being struck between device cost and error recovery overhead.

In one specific example, a line of SAM information may have the mandatory eleven fields and then an additional eight optional tag fields. An exemplary line of SAM input may include, for example, the eleven mandatory fields and eight additional tag fields, for a total of 19 fields.

If a 64-byte hardware parser 106 is used, the threshold number of tags may be six. The maximum number of tags that can fit into a 64-byte chunk of SAM data is 10. Thus, if a given chunk of SAM data includes a seventh tag, the hardware parser 106 may put a special value into the output (e.g., a '−1') with the offset of the SAM file. This may be inserted in-line with the output or may be stored at the top of an output data file to make subsequent review by the software parser 108 simpler. One example for an error field that may be used in a BAM record is the "int32_t block_size" field, where a negative value shows that the record is incomplete. The conversion information may be appended after the tag field, which is a final, variable length field of the BAM record. The information stored therein may include a combination of the SAM field ID that caused a parse error and the data range of the input that was not parsed. The size of the memory space that is allocated in the incomplete BAM record for unparsed data is calculated based on the size of the unparsed input data. The software parser 108 can therefore simply replace the empty portion of the BAM record with the correctly parsed input data.

There may also be a threshold value for the number of digits in a particular field. The sixth mandatory field in SAM, for example, is the "CIGAR" field and may include a long string of characters. The threshold may therefore indicate the maximum size of a particular field that can be handled by the hardware processor 106.

Figure 3:
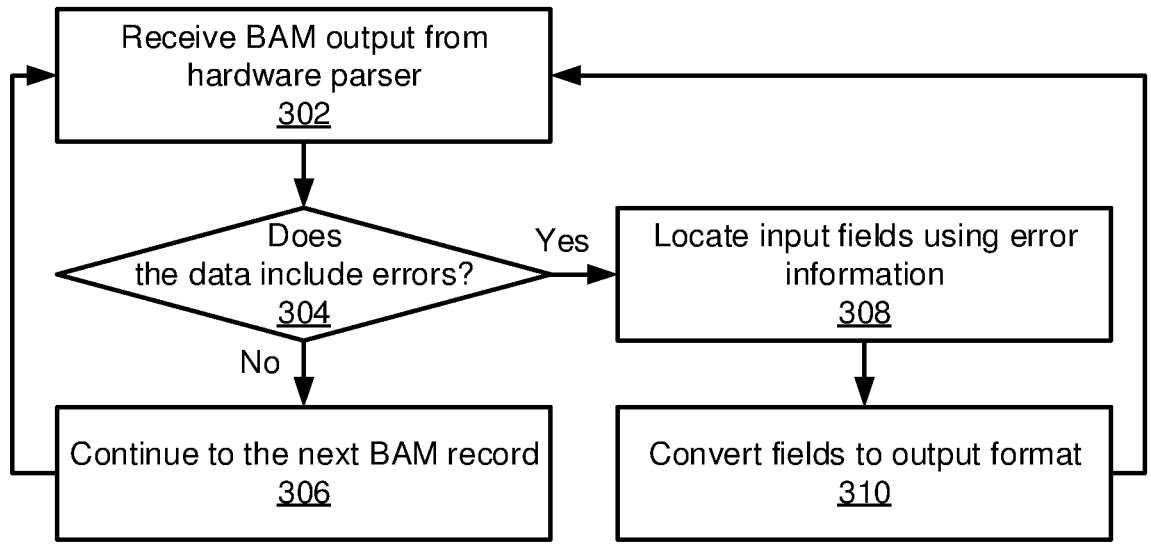
FIG. 3 is a block/flow diagram of a method for second-stage parsing of SAM input information in accordance with embodiments of the present invention.

Referring now to FIG. 3, a method of further parsing the output of the hardware parser 106 is shown. As described above, the hardware parser 106 may encounter input lines that are too big for it to accommodate. In such cases, the hardware parser 106 embeds error information in the output. Block 302 receives the output of the hardware parser 106. In one embodiment that output may be in a BAM format or BAM-with-errors.

Block 304 determines whether a particular block of data from the hardware parser 106 includes embedded error information. This embedded error information indicates where in the original input the error occurred. If no errors are present, block 306 continues to the next BAM record. If errors are present, block 308 locates the input fields from the first format in storage 104 and block 310 converts those fields to the output format. The conversion may be performed in software, as described above. Processing then returns to block 302 to receive the next piece of output from the hardware parser 106.

The methods of FIG. 2 and FIG. 3 work in conjunction to process the entirety of the input stream from the gene sequencer 102. In many cases, where the additional information included in the fields of the SAM lines does not exceed the capacity of the hardware parser 106, the software parser 108 need not be engaged at all. Furthermore, the method of FIG. 3 need not be performed at the same physical location as the method of FIG. 2. Instead, the output of FIG. 2 may be stored or transmitted to a separate location or device, where the software parser 108 reviews that output to correct for any errors that may have occurred.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 4:
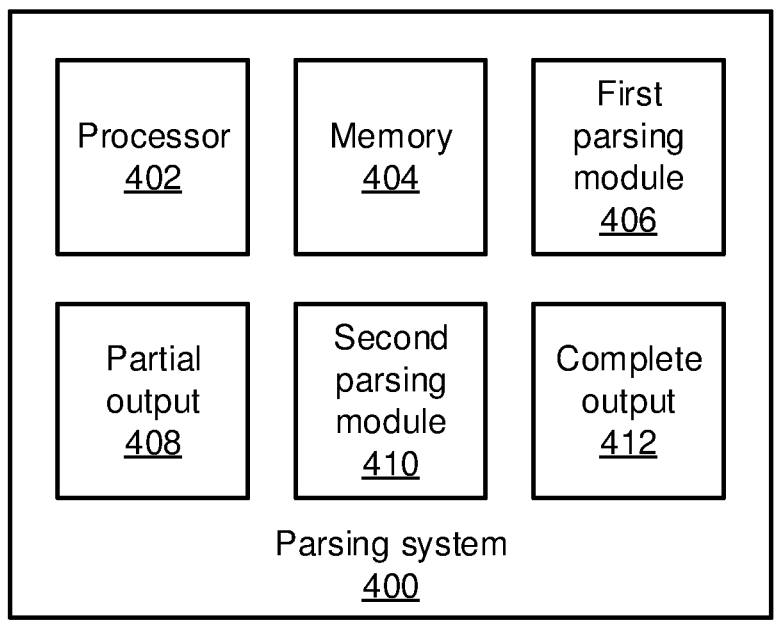
FIG. 4 is a block diagram of a system for parsing SAM input information in accordance with embodiments of the present invention.

Referring now to FIG. 4, a parsing system 400 is shown. The parsing system 400 includes a hardware processor 402 and memory 404. The parsing system 400 also includes one or more functional modules that, in one embodiment, may be implemented as software that is stored in the memory 404 and is executed by the hardware processor 402. In alternative embodiments, one or more of the functional modules may be implemented as one or more hardware components in the form of, e.g., FPGAs or application specific integrated chips.

In particular, the system 400 includes a first parsing module 406 and a second parsing module 410. Although the present description focuses on a hardware implementation of the first parsing module, in particular embodied as an FPGA, it should be understood that two-stage parsing is also contemplated where both stages are performed by software that is executed on the hardware processor 402. The first parsing module 406 parses an input in a first format and provides a partially parsed output 408 that includes, e.g., error information indicating that certain portions of the input data were not parsed and information regarding the location of those portions. A second parsing module 410 then assesses the partial output 408 and replaces those sections of the partial output having errors with correctly parsed information, producing a complete output 412. It should be understood that the partial output 408 and the complete output 412 may be stored in memory 404 or may be streamed to the next component (e.g., the second parsing module 410 or a downstream processing component) directly.

Figure 5:
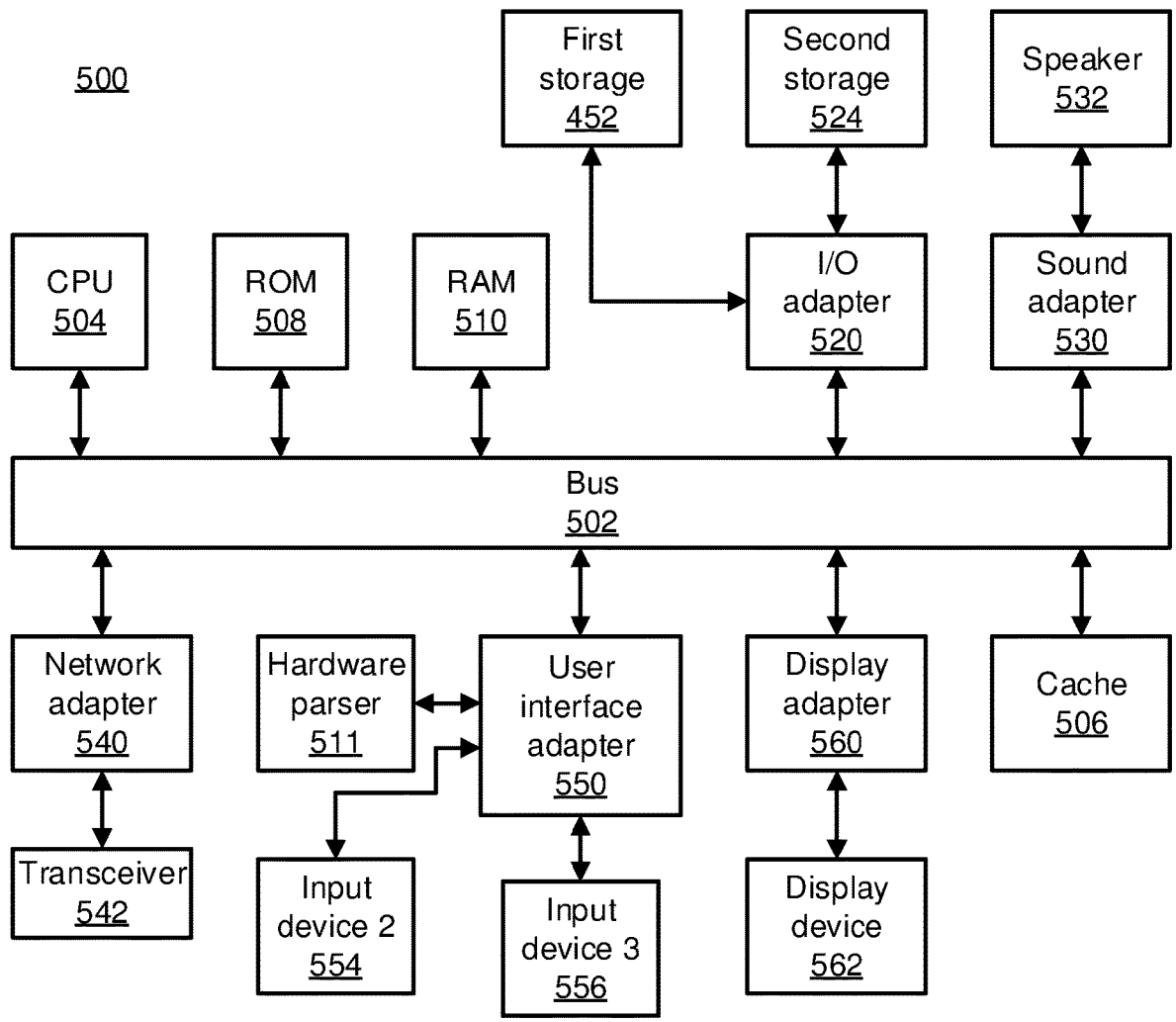
FIG. 5 is a block diagram of a processing system in accordance with embodiments of the present invention.

Referring now to FIG. 5, an exemplary processing system 500 is shown which may represent or include the parsing system 400. The processing system 500 includes at least one processor (CPU) 504 operatively coupled to other components via a system bus 502. A cache 506, a Read Only Memory (ROM) 508, a Random Access Memory (RAM) 510, an input/output (I/O) adapter 520, a sound adapter 530, a network adapter 540, a user interface adapter 550, and a display adapter 560, are operatively coupled to the system bus 502. A hardware parser 511 provides hardware acceleration for specific parsing functions, converting at least part of an input data set from a first format into a second format.

A first storage device 522 and a second storage device 524 are operatively coupled to system bus 502 by the I/O adapter 520. The storage devices 522 and 524 can be any of a disk storage device (e.g., a magnetic or optical disk storage device), a solid state magnetic device, and so forth. The storage devices 522 and 524 can be the same type of storage device or different types of storage devices.

A speaker 532 is operatively coupled to system bus 502 by the sound adapter 530. A transceiver 542 is operatively coupled to system bus 502 by network adapter 540. A display device 562 is operatively coupled to system bus 502 by display adapter 560.

A first user input device 554 and a second user input device 556 are operatively coupled to system bus 502 by user interface adapter 550. The user input devices 554 and 556 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 554 and 556 can be the same type of user input device or different types of user input devices. The user input devices 554 and 556 are used to input and output information to and from system 500.

Of course, the processing system 500 may also include other elements (not shown), as readily contemplated by one of skill in the art, as well as omit certain elements. For example, various other input devices and/or output devices can be included in processing system 500, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 500 are readily contemplated by one of ordinary skill in the art given the teachings of the present principles provided herein.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for accelerated input data conversion, comprising:
generating an intermediate output including unparsed portions of an input data set and parsed portions of the input data set, the parsed portions of the input data set corresponding to portions of the input data set having a size less than a threshold size determined by available resources; and parsing the unparsed portions of the input data set in the intermediate output using a processor to generate a final output such that a combined parsing time for generating the intermediate output and the parsing time to generate the final output is accelerated relative to a single-stage parsing.

2. The method of claim 1, further comprising embedding a marker in the intermediate output indicating a location of the unparsed portion in the input data set.

3. The method of claim 2, wherein embedding the marker in the intermediate output comprises embedding a negative number in a final, variable length field of a record in the output format.

4. The method of claim 2, wherein parsing the unparsed portions of the input data set in the intermediate output comprises locating unparsed information in the input data set based in the indicated location.

5. The method of claim 1, wherein generating the intermediate output is performed using a dedicated hardware component and wherein parsing the intermediate output is performed using software executed by the processor.

6. The method of claim 1, wherein the input data set is genomic data having a sequence alignment/map (SAM) format.

7. The method of claim 6, wherein the threshold size corresponds to a number of SAM fields in a portion of the genomic data.

8. The method of claim 6, wherein the threshold size corresponds to a size of a SAM field in a portion of the genomic data.

9. The method of claim 1, wherein a size of the intermediate output, including the unparsed portions, is allocated based on a size of the unparsed input data set.

10. A non-transitory computer readable storage medium comprising a computer readable program for parsing an input, wherein the computer readable program when executed on a computer causes the computer to perform the steps of claim 1.

11. A method for accelerated input data conversion, comprising:

generating an intermediate output including unparsed portions of an input data set having a sequence alignment/map (SAM) format, and parsed portions of the input data set, the parsed portions of the input data set corresponding to portions of the input data set having a size less than a threshold size determined by available resources, wherein a size of the intermediate output, including the unparsed portions, is allocated based on a size of the input data set;

embedding a marker in the intermediate output indicating a location of the unparsed portions in the input data set; and parsing the unparsed portions of the input data set in the intermediate output using a software processing module executed by a hardware processor to generate a final output such that a combined parsing time for generating the intermediate output and the parsing time to generate the final output is accelerated relative to a single-stage parsing.

12. A system for accelerated input data conversion, comprising:

a first parsing module comprising a hardware processor configured to generate an intermediate output including unparsed portions of an input data set and parsed portions of the input data set, the parsed portions of the input data set corresponding to portions of the input data set having a size less than a threshold size determined by available resources; and a second parsing module configured to parse the unparsed portions of the input data set in the intermediate output using a software processor to generate a final output such that a combined parsing time for generating the intermediate output and the parsing time to generate the final output is accelerated relative to a single-stage parsing.

13. The system of claim 12, wherein the first parsing module is further configured to embed a marker in the intermediate output indicating a location of the unparsed portion in the input data set.

14. The system of claim 13, wherein the first parsing module is further configured to embed a negative number in a final, variable length field of a record in the output format.

15. The system of claim 13, wherein the second parsing module is further configured to locate unparsed information in the input data set based on the indicated location.

16. The system of claim 12, wherein the first parsing module consists of a dedicated hardware component and wherein the second parsing module consists of software executed by a hardware processor.

17. The system of claim 12, wherein the input data set is genomic data having a sequence alignment/map (SAM) format.

18. The system of claim 17, wherein the threshold size corresponds to a number of SAM fields in a portion of the genomic data.

19. The system of claim 17, wherein the threshold size corresponds to a size of a SAM field in a portion of the genomic data.

20. The system of claim 12, wherein a size of the intermediate output, including the at least one unparsed portion, is allocated based on a size of the unparsed input data set.

* * * * *